United States Patent [19]

Rasmussen

[11] 4,174,401
[45] Nov. 13, 1979

[54] 2-BENZHYDRYLIMINO-IMIDAZOLIDINES

[75] Inventor: Chris R. Rasmussen, Ambler, Pa.

[73] Assignee: McNeil Laboratories, Incorporated, Ft. Washington, Pa.

[21] Appl. No.: 815,393

[22] Filed: Jul. 13, 1977

[51] Int. Cl.$^2$ .................. A61K 31/415; C07D 233/44
[52] U.S. Cl. ........................ 424/273 R; 260/239 BC; 546/330; 548/315; 424/244; 424/251
[58] Field of Search ........................ 548/315; 424/273

[56] References Cited

PUBLICATIONS

Daiichi, Japanese Unexamined Pat. Appln. 51–080803, Pub. 15–07–76 Derwent Jap. Patents Rep. Week x35 Sec. B; Pharm. p. 4.

Primary Examiner—Donald G. Daus
Assistant Examiner—D. B. Springer
Attorney, Agent, or Firm—Alice O. Robertson

[57] ABSTRACT

Novel 2-benzhydrylimino-1,3-diazacarbocyclic compounds of the formula

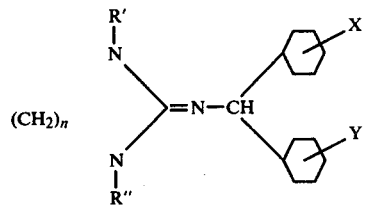

wherein R' and R" independently are selected from the group consisting of hydrogen and methyl, X and Y independently are selected from the group consisting of hydrogen, lower alkoxy, lower alkyl and halo, and n is an integer of from 2 to 4, inclusive; and their acid addition salts are disclosed. Compounds have antisecretory properties. Certain of the compounds also have hypoglycemic properties.

5 Claims, No Drawings

2-BENZHYDRYLIMINO-IMIDAZOLIDINES

SUMMARY OF THE INVENTION

This invention relates to novel diazacarbocyclic compounds, more particularly to 2-benzhydrylimino-1,3-diazacarbocyclic compounds and their acid addition salts. The novel compounds are useful as agents for inhibiting gastric acid secretion. Certain of the compounds are useful as agents for reducing blood sugar. The invention embraces the foregoing uses of the novel compounds.

DESCRIPTION OF THE INVENTION

The novel diazacarbocyclic compounds may be represented by the formula

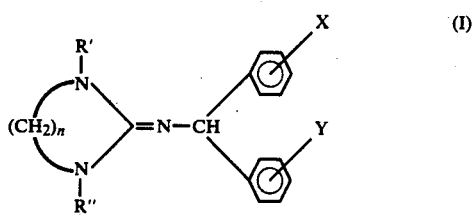

In this and succeeding formulas, R' and R" are radicals independently selected from the group consisting of hydrogen and methyl, X and Y are radicals independently selected from the group consisting of hydrogen, lower alkyl, lower alkoxy and halo, and n is an integer of from 2 to 4, inclusive.

In the foregoing definitions, the expression "lower alkyl" refers to a straight or branched hydrocarbon radical having from 1 to about 5 carbon atoms, such as methyl, ethyl, isopropyl, sec-butyl, pentyl, isoamyl, etc. The expression "lower alkoxy" refers to a straight or branched chain radical in which the hydrocarbon portion has from 1 to about 5 carbon atoms, and which may be represented by groups such as methoxy, ethoxy, isopropoxy, n-propoxy, sec-butoxy, t-butoxy, pentyloxy, isopentyloxy and the like. The expression "halo" refers to any of the halogen groups including chloro, bromo, fluoro and iodo.

When at least one of R' and R" is hydrogen, the diazacarbocyclic compound may be present in the tautomeric form represented by Formula Ia

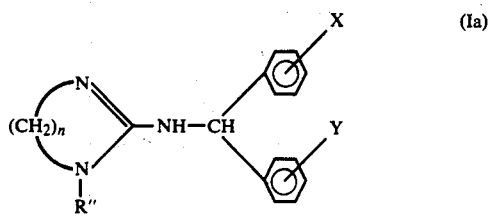

Thus, although the compounds of the present invention are generically named as "imino" compounds, those compounds which can exist in the tautomeric "amino" form are named as amino derivatives.

When X and Y are different groups, the carbon which bears the substituted phenyl groups is an asymmetric carbon and such diazacarbocyclic compounds may be resolved to their optically active isomers, if desired, by conventional procedures. The optically active isomers are considered to be within the scope of the present invention.

The non-toxic, therapeutically acceptable acid addition salts of the diazacarbocyclic compounds are also embraced within the scope of this invention. Suitable acids may be inorganic acids such as hydrochloric, hydrobromic, hydroiodic, phosphoric, nitric and the like acids, or organic acids such as acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic, p-aminosalicylic and the like acids. The preferred addition salts are the hydrohalic addition salts.

The novel 2-benzhydrylimino-1,3-diazacarbocyclic compounds of Formula I as free bases are generally soluble in many common polar and non-polar organic solvents such as aromatic hydrocarbons, e.g., benzene, toluene, and the like; haloaromatic hydrocarbons, e.g., chlorobenzene, 1,2-dichlorobenzene, and the like; haloaliphatic hydrocarbons, e.g., chloroform, methylene dichloride, 1,2-dichlorethane and the like; lower alkanols, e.g., methanol, isopropanol, t-butanol and the like, ethers, e.g., diethyl ether, dioxane and the like, and ketones, e.g., acetone, 2-butanone and the like. They are preferably obtained and employed in the form of their acid addition salts which are generally white crystalline solids soluble in polar solvents such as the lower alkanols, ketones and the like. The compounds possess valuable pharmacological properties, particularly inhibition of gastric acid secretion. Certain of the compounds also have properties suitable for use as hypoglycemic agents.

The diazacarbocyclic compounds may be prepared by reacting an appropriate diamine compound represented by Formula II

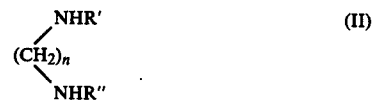

with a thiopseudourea compound, preferably as the hydrogen halide addition salt, represented by Formula III, (and in its tautomeric form as IIIa)

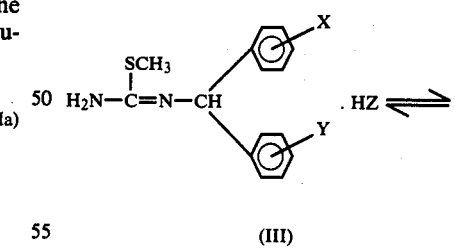

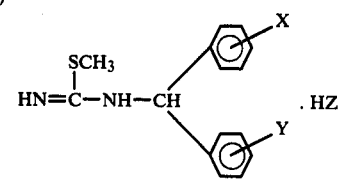

whereupon the desired diazacarbocyclic compound of Formula I is formed in the reaction mixture accompanied by the formation of ammonia and methylmercaptan by-products which are evolved. The preparation of the diazacarbocyclic compounds is preferably carried out in an inert organic solvent, at elevated temperatures, preferably at temperature above 150° C. and employing solvents suitable for providing reflux conditions in the desired temperature range. Preferred solvents include o- and m- dichlorobenzene although somewhat lower boiling solvents such as the xylenes and the like also may be employed. For acceptable yields it is desirable to use substantially equimolar proportions of the reactants.

In carrying out the reaction, the appropriate diamine of Formula II is contacted preferably with stirring with a suspension of the appropriate thiopseudourea hydrohalide of Formula III in a suitable solvent. The mixture of reactants then is heated under refluxing conditons for time sufficient to complete the reaction with the formation of the desired diazacarbocyclic compound in the reaction mixture. The completion of the reaction is evidenced most clearly by cessation in the evolution of ammonia and methylmercaptan by-products. Generally, the reaction takes place over several hours and conveniently the reaction mixture is allowed to reflux overnight to insure completion of the reaction. After completion of the reaction, the desired diazacarbocyclic compound which usually separates as a hydrohalide salt in the form of a solid or oily precipitate is recovered from the reaction mixture by decanting the solvent and purifying the residue by conventional procedures such as washing, treating with activated carbon, recrystallizing and the like. The salt optionally may be converted to the free base or to a different acid addition salt employing conventional procedures as subsequently described.

An alternative method for the preparation of the diazacarbocyclic compounds which are particularly adaptable to the preparation of the imidazoline compounds represented by the formula

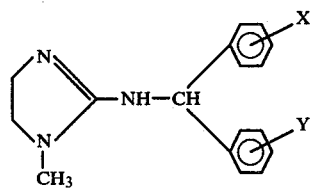

Methylmercaptan is a by-product in this method. While the reaction may be adaptable to be employed for the preparation of larger ring diazacarbocyclic compounds, the more ready availability of the imidazoline starting material renders it particularly suitable for the preparation of the compounds represented by Formula Ib. The reaction is carried out employing substantially equimolar proportions of the reactants. A lower alkanol solvent is preferred as a reaction medium. The most suitable solvents include isopropanol and tert-butanol. The reaction is carried out at somewhat elevated temperatures (about 80°-120° C.) conveniently at reflux temperatures for from about 4 to about 24 hours or until the reaction is substantially complete as evidenced by the cessation of methylmercaptan formation. Conveniently the mixture may be refluxed overnight to insure completion of the reaction.

In carrying out the reaction according to this method, the appropriate imidazoline and appropriate benzhydrylamine and lower alkanol solvent are mixed together and heated at reflux temperature for time sufficient to complete the reaction. After completion of the reaction, the reaction mixture is allowed to cool to room temperature to allow the precipitation of the desired imidazoline compound of Formula Ib as the hydrohalide salt. The product is then recovered preferably by separating the solvent and purified by conventional procedures, such as washing and recrystallization from a polar solvent such as the lower alkanols. The salt optionally may be converted to the free base, and thence to other salt forms.

The diazacarbocyclic compounds represented by the formula

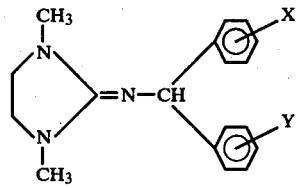

is by the reaction of 1-methyl-2-methylthioimidazoline as its hydrohalide salt with an appropriate benzhydrylamine as seen in the following equation may be prepared by an alternative method wherein a 1,3-dimethyl-2-imidazoline (VI) is first converted to a 2-alkoxyimidazoline fluoborate (VII) with an appropriate trialkyloxonium fluoborate and the intermediate of Formula VII reacted with an appropriate benzhydrylamine of Formula V to obtain the diazacarbocyclic product as a hydrofluoborate salt (Ic') according to the following equation

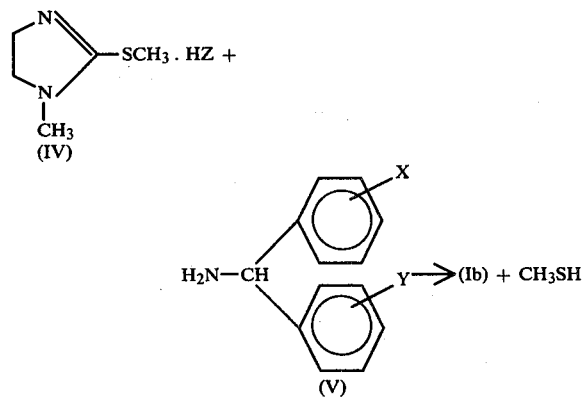

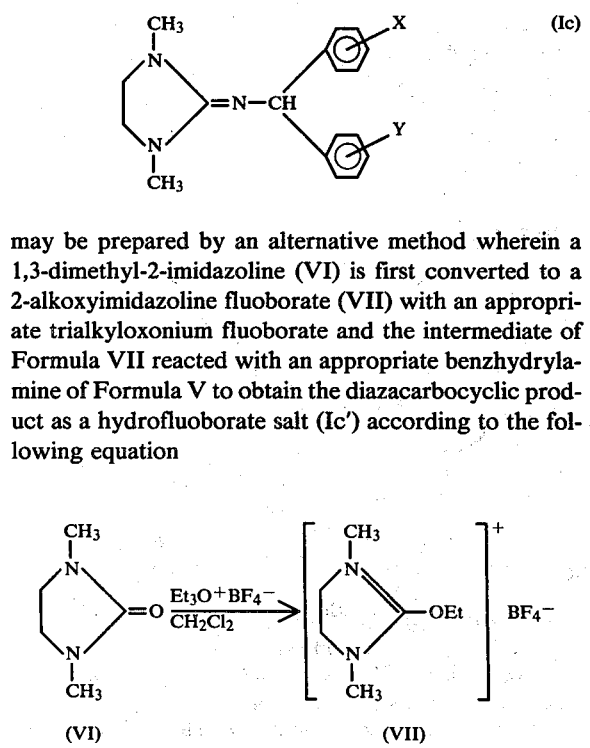

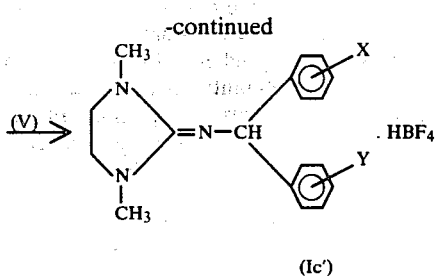

(Ic')

The preparation of the fluoborate intermediate of Formula VII from the 1,3-dimethyl-2-imidazolone may be carried out in a manner similar to that described in Ber. 89, 2063 (1956). The reaction of the intermediate of Formula VII with a suitable benzhydrylamine is preferably carried out at from 0° C. to to ambient temperature under an inert ($N_2$ or Ar) dry atmosphere in inert anhydrous solvents. Preferred solvents are the lower halogenated hydrocarbons such as methylene chloride, 1,2-dichloroethane, chloroform and the like. The reactants are contacted, generally employing substantially stoichiometric quantities, to obtain the product as the hydrofluoborate salt (Ic') which then may be converted to the free base and thence to other acid addition salts.

The diazacarbocyclic compounds of the present invention which are in the salt form, e.g. as the hydrofluoborate salt or as the hydrohalide salt, may be converted to the corresponding free amine bases by conventional means such as by treating a water solution or suspension of the salt with excess amounts of an alkali metal hydroxide or carbonate in the presence of a water-immiscible solvent such as diethyl ether, benzene, toluene, chloroform and the like. The amine bases thus obtained may be converted, if desired, to different acid addition salts by contacting with the appropriate acids, preferably in a solvent such as the lower alkanols, lower ketones, ethers and the like.

The desirable antisecretory properties of the diazacarbocyclic compounds of Formula I and their acid addition salts may be demonstrated with the acute gastric fistula rat test. In the test, determinations for antisecretory activity is carried out in female Sprague-Dawley rats after intraduodenal (i.d.) injection of the compound at doses generally ranging from 2.5–40 mg./kg. body weight. The rats are fasted 24 hours before testing and are given water ad libitum while being kept in individual cages. On the day of testing, the rats are weighed and are selected so that the rats in each test have weights within a range of ±20 grams.

Surgery for the acute gastric fistula test is carried out under light ether anesthesia. As soon as the rat is anesthetized, its teeth are removed using a small pinch pliers. A mid-line incision is made on the abdomen about 1½ centimeters in length and the stomach and duodenum are exposed. If at this point, the stomach is filled with food or fecal material, the rat is discarded. Using 4-0 suture, a purse string stitch is placed on the fundic portion of the stomach taking care not to pierce any blood vessels in the area. A small nick is made into the stomach in the center of the purse string, and a cannula, consisting of a small vinyl tube with a flange on one end, is put into the stomach and the purse string stitch is closed tightly around the flange. Immediately following this, the test compound is administered I.D. in a volume of 0.5 milliliter per 100 gram rat. Three rats are generally used for each drug dose tested. Control rats receive the test vehicle, usually 0.5 percent aqueous methyl cellulose.

After administration of the test compound, the abdominal wall and skin are closed simultaneously with three to four 18 millimeter wound clips and a collecting tube is placed on the cannula. Each rat is then placed in a box in which a longitudinal slit has been made to allow the cannula to hang freely and to allow the rat to move about unencumbered. After the rat is allowed to stabilize for 30 minutes, the collection tube on the cannula is discarded and replaced with a clean tube to receive the gastric juice. Collections are made at one hour. At the end of the study, the cannula is removed and the rat is sacrificed.

The sample of gastric contents collected is drained into a centrifuge tube and centrifuged to pack down the sediment. Volumes are read and a 1 milliliter aliquot of the supernatant is put into a beaker containing 10 milliliters of distilled water and is titrated to pH 7 using 0.01N NaOH. Results are determined for Volume, Titratable Acid, and Total Acid Output where Volume=-total milliliter of gastric juice minus sediment; Titratable Acid (milliequivalents/liter)=amount of 0.01N NaOH needed to titrate the acid to pH 7; and Total Acid Output=Titratable Acid×Volume. Results are reported in Percent Inhibition vs. Controls and a minimum of 5 percent Inhibition indicates anti-secretory activity.

The 2-benzhydrylimino-1,3-diazacarbocyclic compounds show antisecretory properties on administration at doses in the range of from about 2.5 mg./kg. to 40 mg./kg. of body weight. In representative tests carried out as above-described with the hydroiodide salts of 2-diphenylmethylamino-1,4,5,6-tetrahydropyrimidine, 2-diphenylmethylamino-4,5,6,7-tetrahydro-1H-1,3-diazepine, 2-diphenylmethylamino-1,4,5,6-tetrahydro-1-methylpyrimidine, 2-diphenylmethylamino-1-methyl-2-imidazoline, and 2-diphenylmethylamino-1,2,3,4,5,6-hexahydro-1,3-dimethylpyrimidine at a dose of 20 mg./kg. and readings made one hour after administration, valuable antisecretory activities were observed with readings of 88 percent, 63 percent, 30 percent, 84.8 percent and 100 percent, respectively.

The compounds represented by the following formula

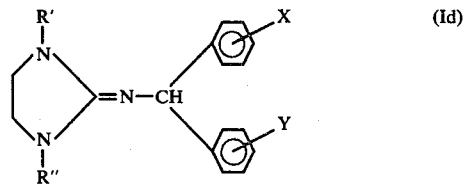

(Id)

especially, where at least one of R' and R" is methyl, are also useful as hypoglycemic agents suitable for lowering blood sugar. This property may be demonstrated by the rat glucose tolerance test, an extremely sensitive standard procedure used in the diagnosis of diabetes and hypoclycemic disease states.

In this test, male Sprague-Dawley rats (Charles River 184-250 grams) are given water ad libitum and fasted 24 hours prior to the experiment. Two to five rats are used for each test and control group. Test Compounds, 1–200 mg./kg., are administered (s.c., i.p. or orally) suspended in 0.5 or 1.0 milliliter, but preferably the former, of 0.5–1.0% methylcellulose vehicle. Control animals are given an equal amount of vehicle. Serial blood samples (0.1 milliliter) are obtained from the tail without anesthesia prior to and at 30, 60, 90, 120, 150 and 180 minutes after administration of 0.8 to 1.0 gram of glucose per kilogram of body weight in 1 milliliter of water. (The glucose is given orally if the test compound has been given parenterally, and subcutaneously if the test compound has been given orally.) Specimens of blood are immediately deproteinized with aqueous solutions of $Ba(OH)_2$ and $ZnSO_4$ and glucose levels are determined using the glucose oxidase assay described by L. P. Cawley et al., "Ultra Micro Chemical Analysis of Blood Glucose with Glucose Oxidase", Amer. J. Clin. Path., 32, 195 (1959). The blood glucose values at each time point are expressed in terms of milligram prcent (mg glucose/100 ml of blood). The mean glucose values of the controls are compared statistically by the Student's t-Test to the means of the experimental group at each of the corresponding time points. If the compound lowers the blood glucose significantly at any time at a 95% confidence limit, the compound is considered to have hypoglycemic activity. The blood glucose lowering, expressed as percent lowering, is obtained by dividing the difference between the mean blood glucose values for test and control animals by the mean glucose value for the control animal.

For reducing blood glucose, the compounds of Formula Id may be employed at a dosage range of from about 0.5 to 100 mg./kg. of body weight. In a representative operation, administration of 2-diphenylmethylamino-1-methyl-2-imidazoline at a dose of 100 mg./kg. (per os) is found to provide a lowering of 50% when compared with controls one-half hour after dosing; administration at a dose of 5 mg./kg. (per os), a lowering of 17% and administration of 1 mg./kg. (per os), a lowering of 11%, both when compared with controls one hour after dosing.

In view of the aforementioned antisecretory activities of the diazacarbocyclic compounds (I) and their acid addition salts, as well as the hypoglycemic activities of certain of the compounds, this invention provides valuable methods and compositions comprising the said compounds as the active ingredient in a pharmaceutically acceptable solvent or carrier and, in addition, it provides an effective method of inhibiting gastric secretion.

To prepare the pharmaceutical compositions of this invention, a 2-benzhydrylimino-1,3-diazacarbocyclic compound or acid addition salt thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg of the active ingredient, and, preferably, from about 10 to about 250 mg.

The foregoing compositions are particularly suitable for use in inhibiting gastric acid secretion by a method comprising internally administering to a gastric hyperacidic subject compositions comprising an effective gastric acid secretion inhibiting amount of a 2-benzhydrylimino-1, 3-diazacarbocyclic compound, preferably as an acid addition salt. The compositions in which the active compound is represented by Formula Id are suitable for use in reducing blood sugar by a method comprising internally administering compositions comprising an effective hypoglycemic amount of the compound of Formula Id, preferably in acid addition salt form.

The following examples illustrate the invention but are not to be construed as limiting.

EXAMPLE I

2-Diphenylmethylamino-1-methyl-2-imidazoline and Its Hydrochloride and Hydroiodide Salts

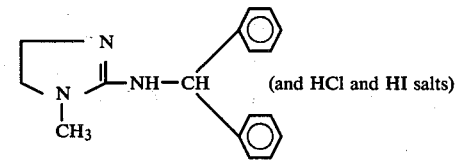

To 7.41 grams (0.10 mole) of N-methylethylenediamine was added 38.43 grams (0.10 mole) of 1-(diphenylmethyl)-2-methyl-2-thiopseudourea hydroiodide in 250 milliliters of o-dichlorobenzene and the resulting mixture allowed to reflux overnight to produce the desired 2-diphenylmethylamino-1-methyl-2-imidazoline product. After completion of the heating, the solvent was removed by decantation and the residue purified by first dissolving in methanol containing activated carbon, replacing the methanol with isopropanol and diluting the isopropanol with acetone-ether to precipitate 16.55 grams (65 percent yield) of 2-diphenylmethylamino-1-methyl-2-imidazoline hydroiodide, m.p. 226°-228° C. After purification by treating with activated charcoal in methanol and recrystallizations from methanol-isopropanol, the product melted at (225°) 227°-229° C.

The hydroiodide product was converted to the free base by suspending in methylene dichloride and intimately admixing with cold 50 percent aqueous sodium hydroxide solution to produce the free base in the mixture. The organic layer containing the free base was decanted, the methylene chloride solution dried over potassium carbonate and the solvent vaporized off to recover 2-diphenylmethylamino-1-methyl-2-imidazoline as residue.

The base thus obtained was dissolved in ether and anhydrous hydrogen chloride added thereto while cooling until the mixture became acidic to obtain a 2-diphenylmethylamino-1-methyl-2-imidazoline hydrochloride product which after recrystallization from methanol-isopropanol melted at (237°) 251°–253° C.

EXAMPLE II

2-Diphenylmethylamino-1,4,5,6-tetrahydro-1-methylpyrimidine Hydroiodide

To 38.43 grams (0.10 mole) of 1-diphenylmethyl-2-methyl-2-thiopseudourea hydroiodide in 270 milliliters of o-dichlorobenzene was added 8.81 grams (0.10 mole) of N-methyl-1,3-diaminopropane, and the resulting mixture was allowed to reflux for about 21 hours to produce the desired 2-diphenylmethylamino-1,4,5,6-tetrahydro-1-methylpyrimidine product. Thereafter, the mixture was allowed to cool, the solvent was decanted off and isopropanol was added to the residue to obtain 35.0 grams (86 percent yield) of a 2-diphenylmethylamino-1,4,5,6-tetrahydro-1-methylpyrimidine hydroiodide salt. After successive recrystallizations from acetone-ether and acetone-isopropanol, a purified product was obtained having a melting point (151°) 169°–171° C.

Anal. Calcd. for $C_{18}H_{21}N_3 \cdot HI$ (279.39/407.30): C, 53.08; H, 5.44. Found: C, 53.00; H, 5.44.

EXAMPLE III

2-Diphenylmethylamino-4,5,6,7-tetrahydro-1H-1,3-diazepine Hydroiodide

A suspension of 38.43 grams (0.1 mole) of 1-diphenylmethyl-2-methylthiopseudourea hydroiodide and 8.82 grams (0.1 mole) of 1,4-diaminobutane in 500 milliliters of o-dichlorobenzene was stirred and heated under reflux overnight (about 19 hours). During the heating a reaction took place with the evolution of a basic gas and methyl mercaptan and the formation of a dark oily layer. While the mixture was still warm, the solvent was decanted from the oily layer, diluted with about 1.5 liters of ether and cooled. Scratching of the ether solution caused light colored crystals to form. The dark oily residue was taken up in about 75 milliliters of isopropanol and stored at −23° C., whereupon it came a semisolid gum; the gum was separated from the mother liquor by decantation and redissolved in fresh isopropanol whereupon a dark solid separated. The light colored crystals from the ether and the dark solid from the isopropanol were separately recrystallized using activated carbon and methanol-isopropanol mixture as solvent to obtain white crystals. The white crystals separately obtained were combined and recrystallized from the same solvent pair to obtain a purified 2-diphenylmethylamino-4,5,6,7-tetrahydro-1H-1,3-diazepine hydroiodide product m.p. 215°–217.5° C.

Anal. Calcd. for $C_{18}H_{21}N_3 \cdot HI$ (279.39/407.30): C, 53.08; H, 5.44; I, 31.16. Found: C, 53.03; H, 5.61; I, 31.04.

EXAMPLE IV

2-Diphenylmethylamino-1,4,5,6-tetrahydropyrimidine Hydroiodide

To 38.43 grams (0.10 mole) of 1-diphenylmethyl-2-methyl-2-thiopseudourea hydroiodide in 25 milliliters of o-dichlorobenzene was added 7.41 grams (0.10 mole) of 1,3-diaminopropane, and the mixture heated (below reflux temperature) for four hours with stirring; then the temperature was increased to reflux temperature and maintained under reflux for 12 hours. The mixture was allowed to cool to room temperature, the solvent decanted off and the residue dissolved in methanol. The methanol solution was concentrated while simultaneously adding isopropanol to obtain 24.6 grams (62.6 percent yield) of 2-diphenylmethylamino-1,4,5,6-tetrahydropyrimidine hydroiodide product, m.p. (185° C.) 197°–200° C. After two recrystallizations from methanol-isopropanol, a purified product of melting point 207°–209° C. was obtained.

Anal. Calcd. for $C_{17}H_{19}N_3 \cdot HI$ (265.36/393.27): C, 51.92; H, 5.13. Found: C, 51.94; H, 5.13.

EXAMPLE V

2-Diphenylmethylimino-1,2,3,4,5,6-hexahydro-1,3-dimethylpyrimidine Hydroiodide

To 38.43 grams (0.10 mole) of 1-diphenylmethyl-2-methyl-2-thiopseudourea hydroiodide in 200 milliliters of o-dichlorobenzene was added 10.22 grams (0.10 mole) of N,N'-dimethyl-1,3-propanediamine and the resulting mixture heated under reflux for 21 hours. The reaction mixture was cooled, the solvent decanted therefrom and isopropanol added to the gummy residue to obtain 24.35 grams (59.8 percent yield) of 2-diphenylmethylimino-1,2,3,4,5,6-hexahydro-1,3-dimethylpyrimidine hydroiodide product of m.p. 215°–219° C. After two recrystallizations from methanol-isopropanol, a purified product, m.p. 221° C., was obtained.

Anal. Calcd. for $C_{19}H_{23}N_3 \cdot HI$ (293.40/421.33): C, 54.17; H, 5.74. Found: C, 54.16; H, 5.76.

EXAMPLE VI

In reactions carried out in a manner similar to that described in the foregoing examples, the following compounds may be prepared:

2-Bis(4-chlorophenyl)methylamino-1-methyl-2-imidazoline hydroiodide by the reaction of N-methylethylenediamine with 1-[bis(4-chlorophenyl)-methyl]-2-methyl-2-thiopseudourea.

2-Bis(2-ethoxyphenyl)methylamino-1-methyl-2-imidazoline hydroiodide by the reaction of N-methylethylenediamine with 1-bis(2-ethoxyphenyl)methyl-2-methyl-2-thiopseudourea.

2-Di(p-tolyl)methylamino-1-methyl-2-imidazoline hydroiodide by the reaction of N-methylethylenediamine with 1-di(p-tolyl)methyl-2-methyl-2-thiopseudourea.

2-Bis(4-methoxyphenyl)methylamino-1,4,5,6-tetrahydro-1-methylpyrimidine hydroiodide by the reaction of N-methyl-1,3-diaminopropane with 1-bis(4-methoxyphenyl)-methyl-2-methyl-2-thiopseudourea.

2-Bis(4-bromophenyl)methylamino-1,4,5,6-tetrahydro-1-methylpyrimidine hydroiodide by the reaction of N-methyl-1,3-diaminopropane with 1-bis(4-bromophenyl)methyl-2-methyl-2-methyl-2-thiopseudourea.

2-Bis(4-chlorophenyl)methylamino-4,5,6,7-tetrahydro-1-methyl-1H-1,3-diazepine hydroiodide by the reaction of N-methyl-1,4-diaminobutane with 1-bis(4-chlorophenyl)methyl-2-methyl-2-thiopseudourea.

2-Bis(2-ethoxyphenyl)methylamino-4,5,6,7-tetrahydro-1-methyl-1H-1,3-diazepine hydroiodide by the reaction of N-methyl-1,4-diaminobutane with 1-bis(2-ethoxyphenyl)methyl-2-methyl-2-thiopseudourea.

(±)2-[α-(3-Bromophenyl)benzylamino]-1-methyl-2-imidazoline hydroiodide by the reaction of N-methylethylenediamine with 1-[α-(3-bromophenyl)benzyl]-2-methyl-2-thiopseudourea.

(±)2-[α-(m-Tolyl)benzylamino]-1,4,5,6-tetrahydro-1-methylpyrimidine hydroiodide by the reaction of N-methyl-1,3-diaminopropane with 1-[α-(m-tolyl)benzyl]-2-methyl-2-thiopseudourea.

(±)2-[α-(4-Iodophenyl)benzylamino]-4,5,6,7-tetrahydro-1-methyl-1H-1,3-diazepine hydroiodide by the reaction of N-methyl-1,4-diaminobutane with 1-[α-(4-iodophenyl)benzyl]-2-methyl-2-thiopseudourea.

EXAMPLE VII

In further reactions carried out in a manner similar to that previously described, the following compounds may be prepared:

2-Bis(4-methoxyphenyl)methylamino-4,5,6,7-tetrahydro-1H-1,3 diazepine hydroiodide by the reaction of 1-[bis(4-methoxyphenyl)]methyl-2-methylthiopseudourea hydroiodide and 1,4-diaminobutane.

(±)2-[(4-Iodophenyl)benzylamino]-4,5,6,7-tetrahydro-1H-1,3-diazepine hydroiodide by the reaction of 1-[(4-iodophenyl)benzyl]-2-methyl-2-thiopseudourea and 1,4-diaminobutane.

2-Bis(4-Bromophenyl)methylamino-1,4,5,6-tetrahydropyrimidine hydroiodide by the reaction of 1-[bis(4-methoxyphenyl)]-methyl-2-methylthiopseudourea hydroiodide and 1,3-diaminopropane.

(±)2-[α-(m-Tolyl)benzylamino]-1,4,5,6-tetrahydropyrimidine hydroiodide by the reaction of 1-[α-(m-tolyl)benzyl]-2-methyl-2-thiopseudourea and 1,3-diaminopropane.

EXAMPLE VIII

In still further reactions carried out in a similar manner, the following compounds may be prepared:

Di(p-tolyl)methylimino-1,2,3,4,5,6-hexahydro-1,3-dimethylpyrimidine hydroiodide by the reaction of 1-di(p-tolyl)methyl-2-methyl-2-thiopseudourea hydroiodide and N,N'-di-methyl-1,3-propanediamine.

Bis(4-chlorophenyl)methylimino-1,2,3,4,5,6-hexahydro-1,3-dimethylpyrimidine hydroiodide by the reaction of 1-bis(4-chlorophenyl)methyl-2-methyl-2-thiopseudourea hydroiodide and N,N'-dimethylethylenediamine.

Bis(4-methoxyphenyl)methylimino-perhydro-1,3-dimethyl-1H-1,3-diazepine hydroiodide by the reaction of 1-bis(4-methoxyphenyl)methyl-2-methyl-2-thiopseudourea hydroiodide and N,N'-dimethyl-1,4-aminobutane.

(±)2-[α-(4-Iodophenyl)benzylimino]-perhydro 1,3-dimethyl-1H-1,3-diazepine hydroiodide by the reaction of 1-[α-(4-iodophenyl)benzyl]-2-methyl-2-thiopseudourea and N,N'-dimethyl-1,4-aminobutane.

2-Diphenylmethylimino-1,3-dimethyl-2-imidazolidine hydroiodide by the reaction of 1-diphenylmethyl-2-methyl-2-thiopseudourea hydroiodide and N,N'-dimethylethylenediamine.

EXAMPLE IX

2-Diphenylmethylamino-1-methyl-2-imidazoline hydroiodide, prepared as described in Example I, is suspended in water and the mixture made basic with sodium hydroxide solution to produce the free base. The aqueous solution is extracted with methylene chloride to recover the free base. The extract is washed with water, dried over potassium carbonate, filtered and concentrated to recover as residue a 2-diphenylmethylamino-1-methyl-2-imidazoline product.

Treatment of the foregoing imidazoline product with hydrobromic acid produces 2-diphenylmethylamino-1-methyl-2-imidazoline hydrobromide.

EXAMPLE X

In operations similar to that described in Examples I and IX, the free bases are prepared from the hydroiodide obtained according to the methods previously described:

2-Diphenylmethylamino-1,4,5,6-tetrahydropyrimidine.

2-Diphenylmethylamino-4,5,6,7-tetrahydro-1H-1,3-diazepine.

2-Diphenylmethylimino-1,2,3,4,5,6-hexahydro-1,3-dimethylpyrimidine.

2-Diphenylmethylamino-1,4,5,6-tetrahydro-1-methylpyrimidine.

2-Diphenylmethylimino-perhydro-1,3-dimethyl-1H-1,3-diazepine.

2-Diphenylmethylimino-1,3-dimethyl-2-imidazolidine.

EXAMPLE XI

In operations similar to that described in Example IX, the free bases are converted to the following acid addition salts by treatment with hydrobromic or hydrochloric acid:

2-Diphenylmethylamino-1,4,5,6-tetrahydropyrimidine hydrobromide.

2-Diphenylmethylamino-4,5,6,7-tetrahydro-1H-1,3-diazepine hydrobromide.

2-Diphenylmethylimino-1,2,3,4,5,6-hexahydro-1,3-dimethylpyrimidine hydrobromide.

2-Diphenylmethylamino-1,4,5,6-tetrahydro-1-methylpyrimidine hydrochloride.

2-Diphenylmethylimino-perhydro-1,3-dimethyl-1H-1,3-diazepine hydrochloride.

2-Diphenylmethylimino-1,3-dimethyl-2-imidazolidine hydrochloride.

EXAMPLE XII 1,3-Dimethyl-2-diphenylmethyliminoimidazolidine

To 3.79 grams (0.027 mole) of boron trifluoride etherate in 3 milliliters of anhydrous ether under dry argon, is added as rapidly as possible while maintaining control of the reaction, 1.8 gram (0.02 mole) of epichlorohydrin in 7 milliliters of dry ether. After about 3 hours, the crystals of triethyloxonium fluoborate which are formed are separated and washed with fresh dry ether under dry argon. The crystals are then dissolved in dry methylene chloride (5 ml.) and a solution of 2.28 grams (0.02 mole) of 1,3-dimethyl-2-imidazolidinone in 25 milliliters of dry methylene chloride is added. After stirring at room temperature for about 3 hours, 3.66 gram (0.02 mole) of benzhydrylamine in 5 milliliters of methylene chloride is added. The resulting mixture is allowed to stir overnight at room temperature. Treatment of the reaction mixture with excess cold (0° C.) 20% NaOH, shaking, and separation of the organic layer gives a solution of the free base. This solution is dried over anhydrous potassium carbonate, filtered and the solvent is vaporized in vacuo to afford the 1,3-dimethyl-2-diphenylmethyliminoimidazolidine product.

EXAMPLE XIII

2-Diphenylmethylamino-1-methyl-2-imidazoline Hydroiodide

To 11.91 grams (0.05 mole) of 2-thiomethyl-1-methyl-2-imidazoline hydroiodide in 50 milliliters tert-butanol is added 9.16 (0.05 mole) of benzhydrylamine. The mixture is heated under reflux until evolution of methyl mercaptan ceases. Cooling and dilution with ether affords crystals which are recrystallized from methanol-isopropanol to give the purified 2-diphenylmethylamino-1-methyl-2-imidazoline hydroiodide product of Example I.

The starting materials to be employed in the foregoing processes are either known or readily obtainable from known materials using procedures described in the literature. The diamines (II) are known materials and generally are available commercially. The S-methylbenzhydrylpseudothiouronium salts (III) may be prepared by known methods. Thus, it may be prepared by reacting an appropriate thiourea

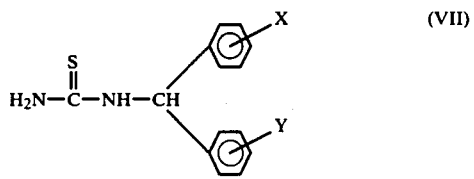
(VII)

with a methylating agent such as methyl iodide, methyl sulfate, methyl tosylate, etc. in the manner described by S. O. Winthrop et al, J. Am. Chem. Soc. 79 3496 (1957). The thiourea, in turn, may be prepared either (a) by the reaction of an appropriate benzhydrylamine (V) as its addition salt with ammonium thiocyanate in refluxing toluene as described in the foregoing Winthrop et al article or (b) by the reaction of an appropriate benzhydrylisothiocyanate

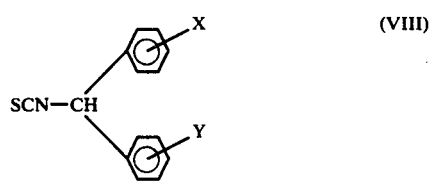
(VIII)

with ammonia, preferably in ethereal solvents such as tetrahydrofuran, dioxane, 1,2-dimethoxyethane and the like at from about 0° C. to ambient temperature. The benzhydrylisothiocyanates (VIII) may be prepared conveniently from the appropriate benzhydrylamine (V) by the method of J. C. Jochims et al, Angew. Chem. Internat. Ed., 6 (2), 174 (1967) carried out by contacting the amine with carbon disulfide and a carbodiimide, for example, dicyclohexylcarbodiimide of the formula

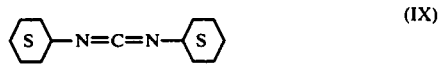
(IX)

in dry ether. The benzhydrylamines are generally well known and may be prepared from various available starting materials by various known procedures such as for example by boiling an oxime of an appropriate ketone with zinc dust and ammonia.

What is claimed is:

1. A compound represented by the formula

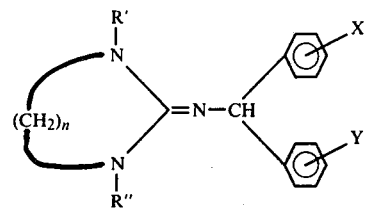

wherein R' and R" independently are selected from the group consisting of hydrogen and methyl, X and Y independently are selected from the group consisting of hydrogen, lower alkoxy, lower alkyl and halo, and n is 2, and the therapeutically active acid addition salts thereof.

2. A compound according to claim 1 which is 2-diphenylmethylamino-1-methyl-2-imidazoline.

3. A method for inhibiting gastric acid secretion which comprises the step of administering to a subject with gastric hyperacidity an effective antisecretory amount of a compound of the formula

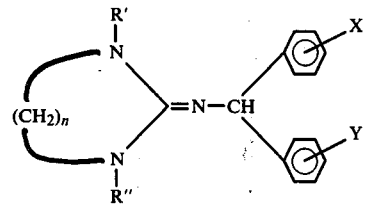

wherein R' and R" independently are selected from the group consisting of hydrogen and methyl, X and Y independently are selected from the group consisting of hydrogen, lower alkoxy, lower alkyl and halo, and n is 2, and the therapeutically active acid addition salts thereof in admixture with a pharmaceutical carrier.

4. A pharmaceutical composition suitable for reducing blood sugar or inhibiting gastric acid secretion in dosage unit form of from about 10 to about 500 milligrams of a compound of the formula

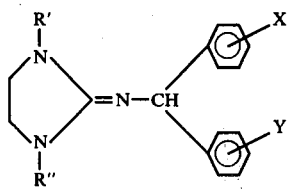

wherein R' and R" independently are selected from the group consisting of hydrogen and methyl, X and Y independently are selected from the group consisting of hydrogen, lower alkoxy, lower alkyl and halo; and the therapeutically active acid addition salts thereof as active ingredients in admixture with a pharmaceutical carrier.

5. A method for reducing blood sugar which comprises the step of administering an effective hypoglycemic amount of a compound of the formula

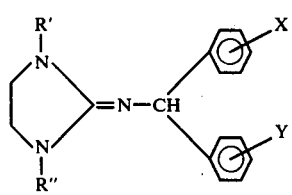

wherein R' and R" independently are selected from the group consisting of hydrogen and methyl, X and Y independently are selected from the group consisting of hydrogen, lower alkoxy, lower alkyl and halo; and the therapeutically active acid addition salts thereof as active ingredient in admixture with a pharmaceutical carrier.

* * * * *